United States Patent [19]
Imran

[11] Patent Number: 5,957,922
[45] Date of Patent: *Sep. 28, 1999

[54] TRANSURETHRAL RADIO FREQUENCY APPARATUS FOR ABLATION OF THE PROSTATE GLAND AND METHOD

[75] Inventor: Mir A. Imran, Palo Alto, Calif.

[73] Assignee: Vidamed, Inc., Fremont, Calif.

[ * ] Notice: This patent is subject to a terminal disclaimer.

[21] Appl. No.: 08/933,622

[22] Filed: Sep. 12, 1997

Related U.S. Application Data

[63] Continuation of application No. 08/653,437, May 24, 1996, abandoned, which is a continuation of application No. 08/285,494, Aug. 3, 1994, Pat. No. 5,520,684, which is a continuation of application No. 08/074,918, Jun. 10, 1993, abandoned.

[51] Int. Cl.$^6$ ..................................................... A61B 17/37
[52] U.S. Cl. .............................. 606/41; 606/42; 607/102; 607/105
[58] Field of Search .................. 606/29–31, 41, 606/42, 45–50; 607/100–105, 122

[56] References Cited

U.S. PATENT DOCUMENTS

| | | | |
|---|---|---|---|
| Re. 33,925 | 5/1992 | Bales et al. | 606/48 |
| 4,682,596 | 7/1987 | Bales et al. . | |
| 4,765,311 | 8/1988 | Petruzzi et al. . | |
| 4,940,064 | 7/1990 | Desai | 607/122 |
| 5,009,656 | 4/1991 | Reimels . | |
| 5,057,105 | 10/1991 | Malone et al. | 606/28 |
| 5,220,927 | 6/1993 | Astrahan et al. . | |
| 5,281,213 | 1/1994 | Milder et al. | 607/122 |
| 5,342,357 | 8/1994 | Nardella | 606/48 |
| 5,348,554 | 9/1994 | Imran et al. | 606/41 |
| 5,403,311 | 4/1995 | Abele et al. | 606/49 |
| 5,462,521 | 10/1995 | Brucker et al. | 606/46 |
| 5,520,684 | 5/1996 | Imran | 606/41 |

FOREIGN PATENT DOCUMENTS 16901786  6/1989  U.S.S.R. .................................. 606/41

*Primary Examiner*—Michael Peffley
*Attorney, Agent, or Firm*—Flehr Hohbach Test Albritton & Herbert LLP

[57] ABSTRACT

A transurethral radio frequency apparatus for ablation of the prostate gland through the urethra formed by a wall, a probe consisting of a flexible elongate tubular member with proximal and distal extremities and sized so as to be adapted to be inserted into the urethra, and an ablation electrode carried by the distal extremity of the flexible elongate member. The flexible elongate tubular member is provided with first and second flow lumens for delivering a cooled fluid to the ablation electrode to cool the same. Means are connected to the probe to supply a coolant solution to the probe, to supply radio frequency energy to the electrode while it is being cooled, and to monitor the temperature of the ablation electrode so that the ablation electrode is maintained at a temperature below a predetermined temperature to spare the urethral wall from irreversible damage from the radio frequency energy delivered to the ablation electrode.

11 Claims, 2 Drawing Sheets

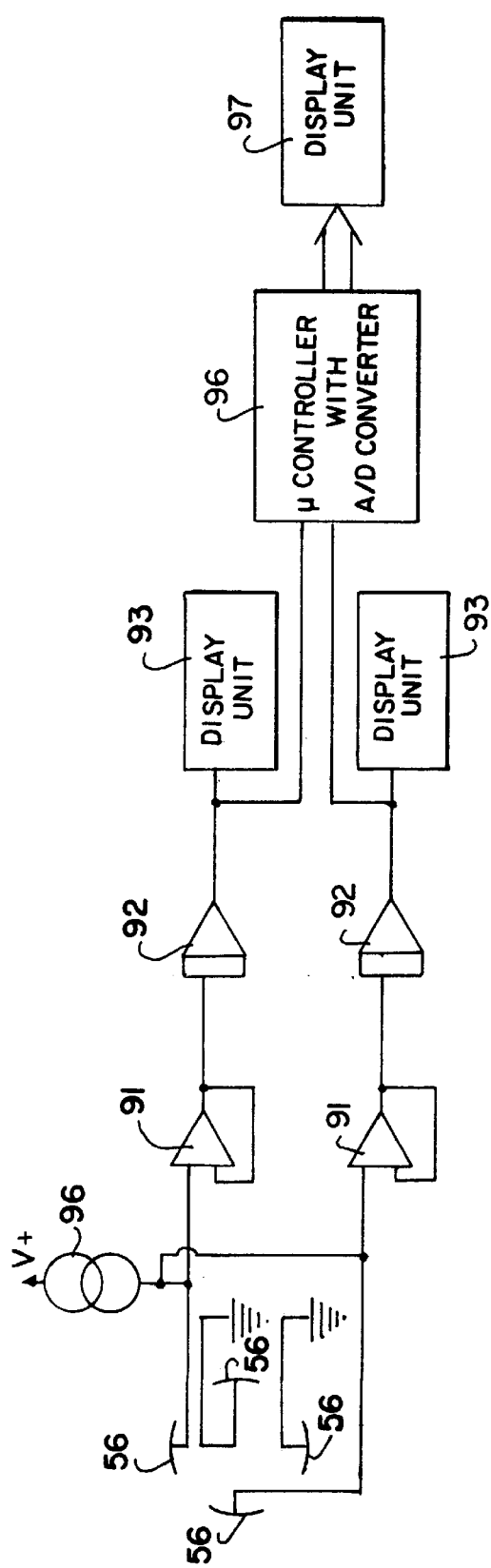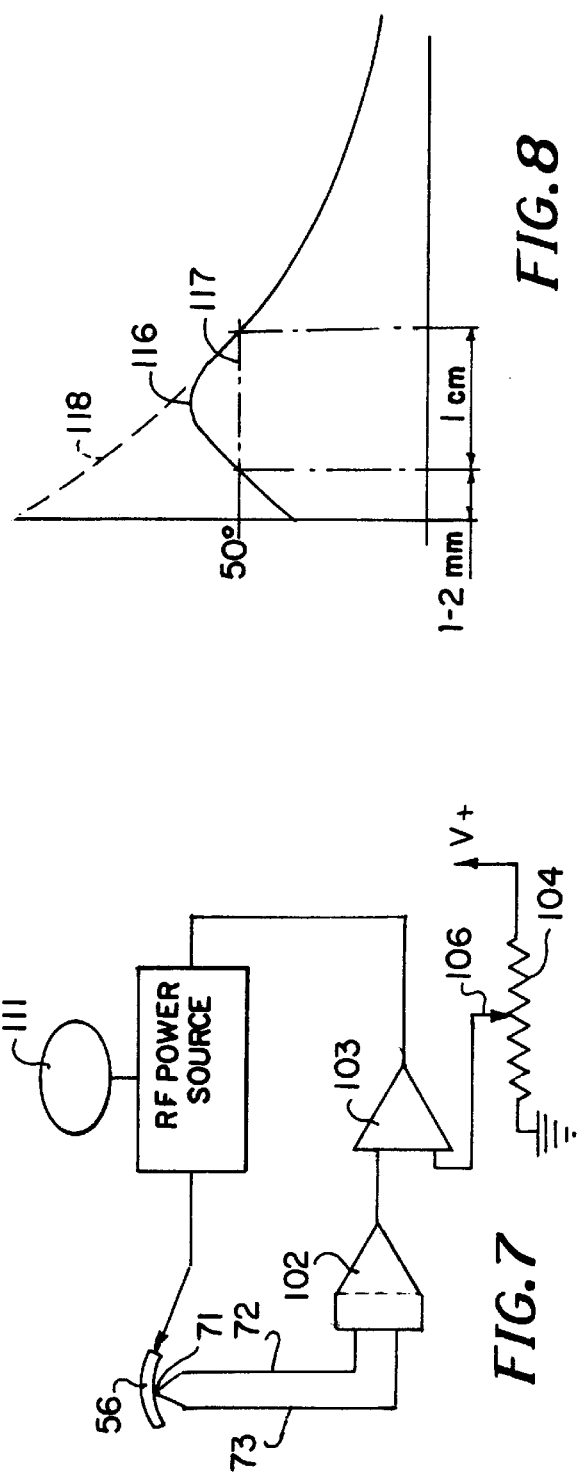

TRANSURETHRAL RADIO FREQUENCY APPARATUS FOR ABLATION OF THE PROSTATE GLAND AND METHOD

This is a continuation of application Ser. No. 08/653,437 filed May 24, 1996 (now abandoned) which is a continuation of application Ser. No. 08/285,494 filed Aug. 3, 1994, now U.S. Pat. No. 5,520,684, which is a continuation of application Ser. No. 08/074,918 filed Jun. 10, 1993, abandoned.

This invention relates to a transurethral radio frequency apparatus for ablation of the prostate gland and method.

Heretofore apparatus and methods have been provided which have been utilized for ablating or destroying tissue in the prostate gland to overcome certain effects of an enlarged prostate gland typically called benign prostatic hypertrophy. Such apparatus and methods have utilized catheters for performing microwave and radio frequency ablation. However, such procedures have typically used a resection of the urethra or have caused a penetration of the urethral wall or damage to the urethral wall at the time that the ablation of the prostatic gland is taking place. Such techniques have often required utilization of an ultrasound viewing instrument to visualize the location of the prostate gland and to aid in locating the distal extremity of the catheter in the prostate gland. There is therefore a need for a new and improved apparatus and method which overcomes these disadvantages.

In general, it is an object of the present invention to provide a transurethral radio frequency apparatus for ablation of the prostate gland and method.

Another object of the invention is to provide an apparatus and method of the above character and in which ablation can be carried without destroying the urethral wall.

Another object of the invention is to provide an apparatus and method which dispenses with the need for ultrasonic viewing.

Another object of the invention is to provide an apparatus and method of the above character in which an ablation electrode is carried by the distal extremity of a catheter disposed in the urethra.

Another object of the invention is to provide an apparatus and method of the above character in which temperature sensing means is provided for sensing the temperature of the ablation electrode.

Another object of the invention is to provide an apparatus and method of the above character in which a cooled ablation electrode is provided.

Another object of the invention is to provide an apparatus and method in which the cooled ablation electrode is provided to preserve the urethral wall and also to enable an increase in the depth of the lesions which can be created.

Another object of the invention is to provide an apparatus and method in which is possible to determine the position of the distal extremity of the catheter within the prostate gland without the use of ultrasound.

Another object of the invention is to provide an apparatus and method of the above character in which impedance sensing means is carried by the distal extremity of the catheter to ascertain when the distal extremity is entering the area of the prostate gland.

Another object of the invention is to provide an apparatus and method of the above character in which the impedance sensing is utilized for controlling the application of radio frequency energy to the ablation electrode.

Additional objects and features of the invention will appear from the following description in which the preferred embodiments are set forth in detail in conjunction with the accompanying drawing.

FIG. 6 is a schematic diagram of the impedance sensing circuitry utilized in the apparatus shown in FIG. 1.

FIG. 7 is a schematic diagram of the radio frequency power circuit utilized for the apparatus shown in FIG. 1.

FIG. 8 is a graph showing the temperatures encountered during an ablation procedure in the prostate gland.

Figure 1:
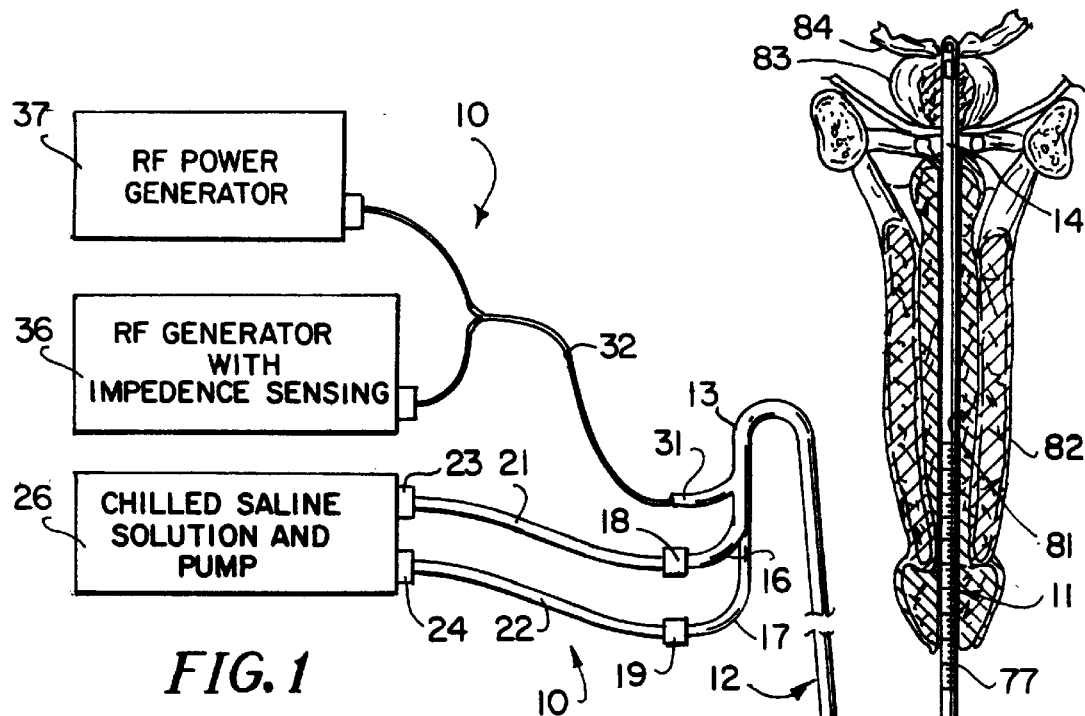
FIG. 1 is a schematic illustration of an apparatus incorporating the present invention showing the apparatus being utilized to perform ablation in the prostate gland.

In general, the radio frequency apparatus for ablation of the prostate gland through the urethra consists of a probe in the form of a flexible elongate member having proximal and distal extremities and adapted to be inserted into the urethra. An ablation electrode is carried by the distal extremity of the flexible elongate member. The flexible elongate member is provided with a first flow passage therein for delivering a cooled fluid to the ablation electrode to cool the same. The flexible elongate member also is provided with an additional flow passage for withdrawing the cooled fluid after it has passed into close proximity of the ablation electrode. Means is connected to the ablation electrode for supplying radio frequency energy to the electrode while it is being cooled to supply radio frequency energy through the urethral wall to the tissue of the prostate gland. The cooling of the ablation electrode serves to protect the urethral wall from the heat generated by radio frequency energy. Impedance sensing means is carried by the distal extremity of the flexible elongate member for ascertaining when the distal extremity of the flexible elongate member has passed into the prostate gland.

More in particular, the transurethral radio frequency apparatus 10 for ablation of the prostate gland consists of a probe 11 which includes flexible elongate member 12 formed of a suitable material such as plastic and having proximal and distal extremities 13 and 14. The proximal extremity 13 is provided with first and second legs 16 and 17 which are connected by fittings 18 and 19 to flexible tubes 21 and 22. The tubes 21 and 22 are connected to fittings 23 and 24 mounted on a block 26 representing schematically a chilled saline solution and pump. The chilled saline solution and pump 26 is utilized for supplying a suitable cooling liquid, as for example a saline solution under pressure through the tubing 21 with a return provided by the tubing 22.

The proximal extremity 13 is also provided with a branch 31 from which there extends a cable 32 for carrying a plurality of conductors as hereinafter described which are connected to a radio frequency generator with impedance sensing capabilities as represented by the block 36.

The flexible elongate tubular member 12 is provided with a central flow lumen 41 which is adapted to receive the cooled saline solution supplied through the tubing 21. The flexible elongate tubular member 12 is also provided with two additional moon-shaped or crescent-shaped lumens 42 and 43 with lumen 42 being used as a return lumen for the saline solution and lumen 43 serving as a wire lumen. A sleeve 46 formed of a suitable conductive material such as platinum or stainless steel and having generally the same diameter as the diameter of the flexible elongate tubular member 12 is secured to the distal extremity 14 by a suitable means such as an adhesive (not shown). The sleeve 46 is provided with a central bore 47 extending therethrough. As shown particularly in FIG. 2, the central flow lumen 41 runs into the bore 47 so that the cooled saline solution exiting therefrom exits near the distal extremity of the sleeve 46. Thereafter it passes proximally as indicated by the arrows 48, past the interior surface of the sleeve 46 and in contact therewith and thence into the return lumen 42 which is in communication with the bore 47.

The hemispherical tip 51 is formed of a suitable material such as plastic and is secured to the distal extremity of the sleeve 46 by suitable means such as a mounting block 52 also formed of plastic and secured to the distal extremity of the sleeve 46 by a suitable means such as an adhesive (not shown).

At least two and preferably four impedance sensing electrodes 56 are carried by the hemispherical tip 51 and as shown are embedded therein and are separated circumferentially by 90° with respect to each other. The impedance sensing electrodes 56 also can be formed of a suitable material such as platinum and are connected by insulated conductors 57 extending through holes 58 provided in the mounting block 52 into the bore 47 of the sleeve 46 thence into the wire lumen 43. Although the conductors 57 extend through the bore 57 which is exposed to the cooling solution, the wire lumen 43 is sealed off from the bore 47 by an epoxy plug 61 at the entrance to the wire lumen 43 (see FIG. 2). Another insulated conductor 66 extends through the wire lumen 43 and is connected to the sleeve electrode 46 at a solder joint 67.

Figure 2:
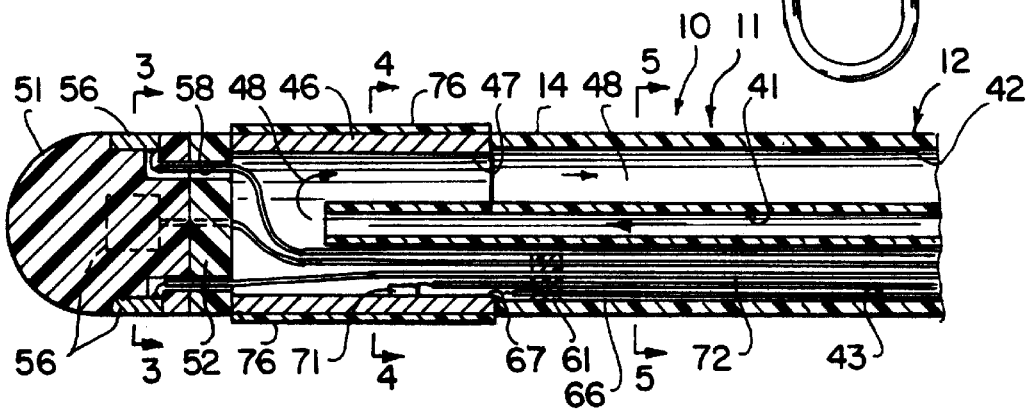
FIG. 2 is an enlarged cross sectional view of a portion of the catheter shown in FIG. 1.
Figure 3:
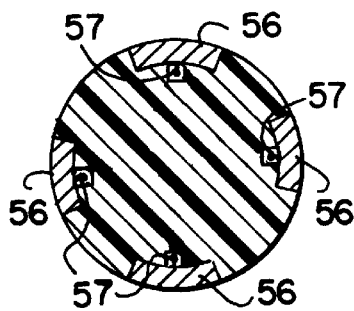
FIG. 3 is a cross-sectional view taken along the line 3—3 of FIG. 2.

Means is provided for sensing the temperature of the sleeve electrode 46 and consists of a thermistor 71 which is disposed adjacent to the inner surface of the sleeve electrode as shown in FIG. 2 and is connected to an insulated conductor 72 which also extends into the wire lumen 43.

Figure 4:
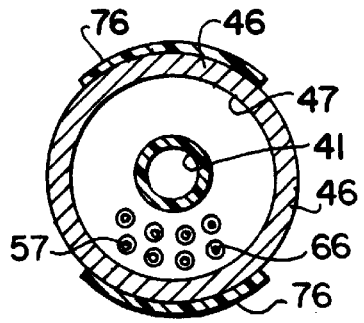
FIG. 4 is a cross-sectional view taken along the line 4—4 of FIG. 2.
Figure 5:
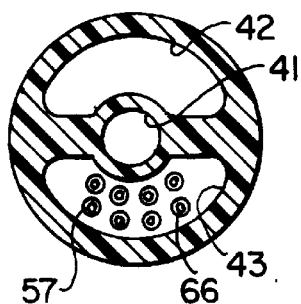
FIG. 5 is a cross-sectional view taken along the line 5—5 of FIG. 2.

Because the prostate gland in which the ablation is to be performed is segmented into two parts disposed on opposite sides of the urethra it may be desirable to provide segmented insulating layers 76 on opposed sides of the sleeve electrode 46 as shown in FIG. 4 so that radio frequency energy will only be radiated from the sleeve electrode 46 in the areas which are the spaced-apart areas between the insulating layers 76.

The probe 11 may be of a suitable size such as 7 to 10 French with a length of 10 to 15 inches. Graduations 77 are provided on the probe and be in centimeters or inches.

Operation and use of the transurethral radio frequency apparatus for ablation of the prostate gland in performance of the method of the present invention may now be briefly described in conjunction with FIGS. 6, 7 and 8. Let is be assumed that a male human being or patient is suffering from benign prostatic hypertrophy which requires medical treatment. The hemispherical tip 51 of the probe 11 is inserted into the urethra 81 of the penis 82 and is advanced progressively until the hemispherical tip 51 carried by the probe 11 is in the vicinity of the prostate gland 83 which is disposed adjacent the bladder 84.

At the commencement of this procedure, the impedance sensing circuitry shown in FIG. 6 of the apparatus 10 is turned on. As shown, the impedance sensing electrodes 56 carried by the hemispherical tip 51 are disposed in two pairs spaced 180° apart with one pair being offset with respect to the other pair by 90°. One electrode of each pair is connected to ground as shown whereas the other electrode is connected to the operational amplifier 91, the output of which is connected to a full wave rectifier 92. The full wave rectifier 92 has its output connected to a display unit 93 which can be in the form of a video display monitor.

A radio frequency constant current source 96 is provided for supplying a very small constant current, less than 10 milliamperes, to each of the ungrounded sensing electrodes 56. The source 66 can be of a suitable frequency, as for example from 100 to 200 KHz. The frequency of the radio frequency from the constant current generator 96 is selected so that it is high enough so that it will not cause any stimulation of the sphincter muscle of the urethra. The current is kept low enough so that there is substantially no heating of the electrodes 56 but still making it possible to measure impedance. The AC voltage which is picked up by the impedance sensing electrode 56 is amplified by the amplifier 91 and supplied to the full wave rectifier 92 and converter to a DC voltage which is displayed on the display unit 93.

Alternatively, the DC output signals from the full wave rectifiers 92 can be supplied to a microcontroller 96 with an A/D converter, the output of which is supplied to a display unit 97. The microcontroller 96 processes the signals from the two sets of sensing electrodes 56 which by a simple algorithm can multiply the two impedances and thereby magnify the change in impedance to obtain a signal which is the square of the impedance measured. Thus a two-to-one change in measured impedance would be represented as a four-to-one change in the display unit 97. It should be appreciated that if only a single set of sensing electrodes is provided that the microcontroller 96 could be provided with an algorithm which would represent a squaring circuit to again magnify a change in impedance.

It has been found that impedance sensing by the use of the impedance sensing electrodes 56 on the hemispherical tip 51 provides a very reliable indicator as to when the hemispherical tip 51 reaches the prostate gland so that the RF electrode 46 can be properly positioned in the prostate gland in the desired position. This is made possible because it has been found that the electrical impedance in the prostate gland is very low compared to the rest of the body, as for example as little as one-half of that of other body tissues such as muscle tissue. It has been found that body fat typically has an impedance ranging from 300–400 ohms and muscle tissue has an impedance ranging from 120–130 ohms whereas the tissue in the prostate gland has an impedance ranging from 50–60 ohms to represent almost a two-to-1 reduction in impedance over that of muscle. This marked reduction in impedance can be readily sensed by the sensing electrodes 56. Thus by observing the display units 93 or the display unit 97 if that is used, it can be readily determined when the hemispherical tip 51 is beginning to enter the prostate gland 83.

Although a single set of sensing electrodes can be provided for measuring impedance, two sets of sensing electrodes have been provided to aid in verifying that a change in impedance has occurred. Thus by way of example, the probe 11 can be rotated by 90° merely by grasping the proximal extremity by the hand and rotating while the probe 11 is in the urethra 81. Thus if a change of impedance is sensed by one of the pair of sensing electrodes, this change in impedance can be verified by rotating the sensing electrodes by 90° to verify that the same change in impedance is sensed by the other set of electrodes. This makes it possible to verify that the entrance to the prostate gland 83 has been reached. After this entrance point or region has been sensed, the probe 11 can be advanced a predetermined distance measured externally on the side 77 on the probe 11 to ensure that the RF sleeve electrode is positioned in the proper position within the prostate gland. This can be readily accomplished since the prostate gland is generally of a known size with the distance being between the opposite extremities of the prostate gland being known so that the RF sleeve electrode can be properly positioned within the prostate gland. In addition, by utilizing the two pairs of sensing electrodes 56 it is possible to position the probe 11 by appropriate rotation of the same externally of the urethra by the hand and to thereby position the probe 11 so that the uninsulated portions of the sleeve electrode 46 extending between the insulating layers 76 are disposed so that they are aligned with the lobes on opposite sides of the prostate gland in which it is desired to introduce radio frequency energy.

During or after the positioning procedure hereinbefore described for the probe 11 has been accomplished, the chilled saline solution and pump apparatus 26 can be turned on so that the chilled saline solution is introduced through the central lumen 41 and passes over the interior of the sleeve electrode 46 and exits through the lumen 42 for at least approximately one minute so as to reduce the temperature of the electrode and the surrounding urethral wall to around 20–25° C. before application of any radio frequency energy from the radio frequency power generator 37. As shown in FIG. 7, the radio frequency power generator 37 consists of a radio frequency power source 101 of a conventional type, as for example, one of a frequency from 400–500 KHz and having a power output capability ranging from 20–30 watts. The source 101 is provided with an output which is connected to the conductor 66 and to the radio frequency electrode 46. The temperature of the radio frequency electrode is sensed by the thermistor 71 which is connected by the conductors 72 and 73 to an amplifier 102. The output of the amplifier 102 is supplied to a comparator 103 which has one input connected to an adjustable temperature setting potentiometer 104 having an adjustable wiper 106. The output from the comparator 103 is supplied to the RF power source 101 to maintain a constant temperature on the radio frequency electrode which is determined as hereinafter described. As is conventional, a dispersive return pad 111 is placed in an appropriate position on the body of the patient to serve as a return for the RF energy in a manner well known to those skilled in the art.

As shown in FIG. 7 as the radio frequency energy is applied to the electrode 46, the temperature gradually increases. Commencing with the point of contact with the wall forming the urethra 81, the temperature gradually increases as shown by the solid curve 116 shown in FIG. 7 until it reaches the broken line power curve 117 shown in FIG. 7. This power curve 117 represents the case of the temperatures which would be encountered if no cooling was being applied to a ablation or sleeve electrode 46. The urethral wall forming the urethra 81 typically has a thickness ranging from 1–2 millimeters as shown by that dimension in FIG. 8. Typically by cooling the radio frequency electrode 46, it is possible to keep the temperature at the urethral wall in the range of 37–40° C. which is well below the temperature at which irreversible damage in human tissue can occur which, for example is typically approximately 50° C. Thus, as shown in FIG. 8, the curve 116 begins to cross the 50° C. broken line 117 at a point which is at the outer margin or slightly beyond the outer margin of the urethral wall represented by the distance of 1–2 millimeters. Thereafter, for a distance of approximately 1 centimeter which is generally the distance in which it is desired to ablate tissue in the prostate gland, the curve 116 representing temperature rapidly rises above 50° C. to cause radio frequency ablation of this tissue. The temperature rises until the curve 116 reaches the broken line curve 118 then gradually decreases to below the 50° C. temperature at a distance of approximately 1 centimeter. Thus irreversible damage in the tissue in the prostate gland will only occur within this region of 1 centimeter from the electrode while sparing the first 1–2 millimeters of tissue which represents the wall of the urethra 81. With such a method it can be seen that it is possible to readily create a lesion ranging in depth from 0.5 to 1 centimeter within the prostate gland depending upon the amount of power applied from the radio frequency source. To ensure that the wall of the urethra 81 will be spared during this ablation procedure, the feedback control hereinbefore described utilizing the thermistor 71 is used to control the radio frequency power source 101 to retain the temperature of the sleeve electrode 46 below 50° C.

It should be appreciated that in connection with the foregoing, automatic controls can be provided with the impedance sensing means hereinbefore described in which the radio frequency power generator 37 can be turned on automatically after a cooling saline solution has been supplied to the electrode for a period of at least one minute to reduce the temperature to the desired level of approximately 25° C. It also should be appreciated that the probe 11 can be rotated during the procedure to achieve additional ablation of the prostate gland if that is desired. After the desired amount of ablation has been achieved, the probe 11 can be readily removed from the urethra 81 to complete the procedure.

It can be seen from the foregoing that there has been provided a transurethral radio frequency apparatus for ablation of the prostate gland and a method by use thereof which makes it possible to achieve such ablation without causing any significant damage to the urethral wall while at the same time making it unnecessary to penetrate the urethral wall and causing damage thereto. In addition, it is possible to perform the method in positioning the probe without the use of ultrasonic imaging means. Thus, there has been provided a relatively simple probe in which positioning and ablation can be accomplished from the same probe.

I claim:

1. A transurethral radio frequency apparatus for ablation of target tissue beyond a wall by the use of radio frequency energy comprising a probe consisting of an elongate tubular member having proximal and distal extremities, a cylindrical sleeve ablation electrode carried by the distal extremity of the flexible elongate member, the flexible elongate tubular member being provided with a first flow lumen in communication with the ablation electrode, cooling means connected to the probe for supplying a cooling fluid to the first flow lumen, means connected to the probe for supplying radio frequency energy to the ablation electrode while it is being cooled, temperature monitoring means for monitoring the temperature of the ablation electrode and means coupled to the temperature monitoring means and to the cooling means for controlling the supply of cooling fluid so that the ablation electrode is maintained at a temperature below a predetermined temperature to spare the wall from irreversible damage while radio frequency energy is being delivered to the ablation electrode to ablate the target tissue.

2. Apparatus as in claim 1 wherein said temperature monitoring means includes means for controlling the application of radio frequency energy to the ablation electrode so that the ablation electrode does not rise above the predetermined temperature.

3. Apparatus as in claim 2 wherein said temperature monitoring means includes automatic means for controlling the temperature so that the temperature of the wall does not exceed a temperature ranging from 37–40° C.

4. Apparatus as in claim 1 wherein the impedance of the target tissue differs from the impedance of the surrounding tissue together with impedance measuring means carried by the distal extremity of the elongate tubular member and providing an electrical signal and means coupled to said electrical signal remote from the probe for displaying the impedance being measured whereby the position of the probe with respect to the target tissue can be ascertained.

5. Apparatus as in claim 4 wherein said impedance measuring means includes first and second pairs of spaced-apart impedance sensing electrodes carried by the distal extremity of the elongate tubular member and means for supplying radio frequency constant current energy of less than 10 milliamperes to the impedance sensing electrodes.

6. Apparatus as in claim 5 wherein at least one pair of said first and second pairs of impedance sensing electrodes includes first and second circumferentially spaced-apart impedance sensing electrodes carried by the distal extremity of the flexible elongate tubular member.

7. Apparatus as in claim 6 wherein the first pair of impedance sensing electrodes is spaced-apart by approximately 90° from the second pair of impedance sensing electrodes.

8. A method for radio frequency ablation of target tissue beyond a wall by the use of a probe having a distal extremity and having a cylindrical sleeve ablation electrode carried by the distal extremity comprising supplying radio frequency energy to the ablation electrode to cause radio frequency energy to be introduced through the wall and into the target tissue and cooling the electrode while radio frequency energy is being applied to the same to maintain the temperature of the electrode at a temperature below 50° C.

9. A method as in claim 8 wherein the temperature of the electrode is maintained at a temperature of approximately 37–40° C.

10. A method as in claim 8 further including the step of sensing the impedance of tissue encountered by the cylindrical sleeve ablation electrode and to determine when a predetermined impedance has been reached and positioning the probe in the tissue in accordance with the predetermined impedance sensed.

11. A method as in claim 10 further including the step of controlling the application of radio frequency power to the electrode to cause ablation of the target tissue to a depth of approximately one centimeter.

* * * * *